United States Patent
Kobayashi (10) Patent No.: US 6,399,858 B1
(45) Date of Patent: Jun. 4, 2002

(54) **CHITINASE GENE FROM *STENOTROPHOMONAS MALTOPHILIA***

(75) Inventor: Donald Kobayashi, North Bergen, NJ (US)

(73) Assignee: Rutgers, the State University, New Brunswick, NJ (US)

( * ) Notice: Subject to any disclaimer, the term of this patent is extended or adjusted under 35 U.S.C. 154(b) by 0 days.

(21) Appl. No.: 09/408,647

(22) Filed: Aug. 26, 1999

Related U.S. Application Data (60) Provisional application No. 60/098,036, filed on Aug. 27, 1998.

(51) Int. Cl.$^7$ .......................... A01H 11/00; C12N 9/16; C07H 21/04
(52) U.S. Cl. ...................... 800/279; 435/195; 536/23.2
(58) Field of Search ........................ 800/279; 536/23.2; 435/195

(56) References Cited

PUBLICATIONS

Fuji T., Multiple domain structure in a chitinase gene (chiC) of Streptomyces livdans, J. Gen. Microbiol. 1993, 139, 677–686.*

Kobayashi, D.Y. 1994. Abstract 139, Phytopathology 84:1081.

Kobayashi, D. and Holtman, M.A. 1997. Abstract, In Proceedings of the Sixth Annual Rutgers Turfgrass Symposium. Center for Turfgrass Science. J. Derr, ed. p. 18.

Kobayashi et al., 1995, Soil Biol. Biochem. 27:1479–1487.

Kobayashi and El–Barrad, 1996, Cur. Microbiol. 32:106–110.

Holtman M.A. and Kobayashi D.Y. 1997. Abstract, Phytopathology 87 (Supplement):S43.

* cited by examiner

*Primary Examiner*—Ponnathapu Achutamurthy
*Assistant Examiner*—Malgorzata A Walicka
(74) *Attorney, Agent, or Firm*—Licata & Tyrrell P.C.

(57) ABSTRACT

A nucleic acid molecule from *Stenotrophomonas maltophilia* is provided, which encodes a novel chitinase enzyme. *Stenotrophomonas maltophilia* strain 34S1, from which an exemplary nucleic acid molecule of the invention was isolated, is also provided. The enzyme, the gene encoding the enzyme, and microorganisms and plants expressing the gene are useful for reducing or preventing plant disease caused by plant pathogenic fungi.

7 Claims, 3 Drawing Sheets

```
        XhoI
   1 CTCGAGGACCATCATGTCCGGGGAACCGTGGTTGGGAACGGGGCCCACCCATTGTACCGAAGTCGGCCGCCGCGGCTTGGCGGCCCGTCGGCACGGCCGCG
 101 CCGTCTTCACGGCCGAACCTTGCGCTGGCTCACGGATTGCCGGACGAATGCATGACAACGTTGTCCTCGCCTGCCCGACCTGCCTTCCGGTCAGGCCCTC
 201 GTCCGCCCCCACTGTTGTTGCCGGCCTCTCCCCGGCGCTCGGACCTGCTGCACGCGGGCCGCCCCACCCGGCGGCCCGCGCCCATCACTAGATCGGAGTA

301 AGACCATGCCTGACCCGATGATGCGCAGTGCGGTGACATCGATATCCCTCCAGCCGGCCGCCCGCCACAAACGCTGGCTGCTTGCCCTCGCCCTGGCGGC
                 M  P  D  P  M  M  R  S  A  V  T  S  I  S  L  Q  P  A  A  R  H  K  R  W  L  L  A  L  A  L  A  A
                                                                                 KpnI        PstI
 401 GGCCGCCACGCCCAGTCTGGCGCTGGCCGCCAACTGTACCGGCGCGCCGGAATGGAACGCCGCAGTGATCTACCTCTCCGGTACCACCCTGCAGAAAGGG
      A  A  T  P  S  L  A  L  A  A  N  C  T  G  A  P  E  W  N  A  A  V  I  Y  L  S  G  T  T  L  Q  K  G

501 GGCGTGCTGTACCGGGCCAACCAGGACATCTGGAATGCCCCGCCCGACCACCCGGCCGGTGCGCCCTACTACACCAACCTGGGCGCCTGCGACGGCAGCG
      G  V  L  Y  R  A  N  Q  D  I  W  N  A  P  P  D  H  P  A  G  A  P  Y  Y  T  N  L  G  A  C  D  G  S  G

601 GCAGCAACCAGCCGCCCACCGTCAGCCTGACCGCCCCCACCGCCGGGGCCAGCTTCACCGCCGGCAGCAGCATCACCGTCAGCGCCAACGCCGCCGACAG
      S  N  Q  P  P  T  V  S  L  T  A  P  T  A  G  A  S  F  T  A  G  S  S  I  T  V  S  A  N  A  A  D  S
                                                                KpnI
 701 CGACGGCAGTGTCAGCAAGGTGGAGTTCTTCCGTGGCGGTACCCTCGCTGGGCATCGACACCAGCGCGCCGTACAGCGTGACCTGGGCCAATGCATCGGCC
      D  G  S  V  S  K  V  E  F  F  R  G  G  T  S  L  G  I  D  T  S  A  P  Y  S  V  T  W  A  N  A  S  A

801 GGCAGCCACACCTTCAAGGCGGTGGCCACCGACAACAACAACGCGGTCACTTCCTCGGCCACGGTCAGCGTGACCGTCACCGCCTCCAGCAACGACACCA
      G  S  H  T  F  K  A  V  A  T  D  N  N  N  A  V  T  S  S  A  T  V  S  V  T  V  T  A  S  S  N  D  T  T

901 CCCCGCCCAGCGTGCCCGGCGGCCTGGCCTCACCCTCCAAAACCGCCACCACGGTCAACCTGGTCTGGAGCGCGGCCACCGACAACAGCGGCGGCAGTGG
      P  P  S  V  P  G  G  L  A  S  P  S  K  T  A  T  T  V  N  L  V  W  S  A  A  T  D  N  S  G  G  S  G

1001 CGTGGCCGGCTACGACGTGTACCGCAACGGCAGCCTGGTCGGCTCACCCAGCGCCACCCAGTACACCGACGGCGGGCTCACCGCCAGCACGGCCTACACC
      V  A  G  Y  D  V  Y  R  N  G  S  L  V  G  S  P  S  A  T  Q  Y  T  D  G  G  L  T  A  S  T  A  Y  T

1101 TACACCGTACGTGCCCGCGACAACGCCGGCAATGCCTCGGCGCAGAGCGGCTCGATCAGCGTGACCACCGCGGCCGGCGGCGGGGGCGGCGGCACCAAGC
      Y  T  V  R  A  R  D  N  A  G  N  A  S  A  Q  S  G  S  I  S  V  T  T  A  A  G  G  G  G  G  T  K  R

1201 GGGTGATCGGCTACTTCACCCAGTGGGGCATCTACGGGCGCAACTACCGGGTCAAGAACATCGACACCAGCGGTTCGGCGGCCAAGCTGACCCACATCAA
      V  I  G  Y  F  T  Q  W  G  I  Y  G  R  N  Y  R  V  K  N  I  D  T  S  G  S  A  A  K  L  T  H  I  N

1301 CTACGCCTTCGGCAACGTGCGCAACAACCGCTGCGAAGTGGGCGTGACCCAGGCCTCCGACCCGAACACCGGCGTCGGCGGGGATGCGTTCGGCGACTAC
      Y  A  F  G  N  V  R  N  N  R  C  E  V  G  V  T  Q  A  S  D  P  N  T  G  V  G  G  D  A  F  A  D  Y

1401 ACCAAGGCCTTCGGTGCCGGCGAGAGCGTCAGCGGCAGCGCCGACACCTGGGACCAGCCGTTGCGCGGCAATTGGAACCAGCTCAAGCAGCTCAAGGCCA
      T  K  A  F  G  A  G  E  S  V  S  G  S  A  D  T  W  D  Q  P  L  R  G  N  W  N  Q  L  K  Q  L  K  A  K

1501 AGCACCCCGAACGTGAAGGTGCTGATCTCGCTGGGTGGCTGGACCTGGTCGCGGTTCTCCAGCGCGGCGCAGCCGGCCAACCGCCAGGCCTTCGTGGCC
      H  P  N  V  K  V  L  I  S  L  G  G  W  T  W  S  R  G  F  S  S  A  A  Q  P  A  N  R  Q  A  F  V  A

1601 CTCGTGCGTGGATGCCTACATCAAGGGCAACCTGCCGGTGACCGACGGCGCCGGTGGCGTGGGCGCGGCAGCGGGCGTGTTCGACGGCATCGACATCGAC
      S  C  V  D  A  Y  I  K  G  N  L  P  V  T  D  G  A  G  G  V  G  A  A  A  G  V  F  D  G  I  D  I  D

1701 TGGGAATACCCGGTAGCGTGCGGGCTGAGCTGCGGCACCCCGGCCGACAACGCCAACTACACCGCGCTGCTGGCCGAGTTCCGCCGCCAGCTGGACGCGG
      W  E  Y  P  V  A  C  G  L  S  C  G  T  P  A  D  N  A  N  Y  T  A  L  L  A  E  F  R  R  Q  L  D  A  V

1801 TGCGGCCCCGGGCTGCTGCTGACGGTGGCGGTGGGCGCGGGGATCGACAAGATCCGCGTGACCGACCCGGCGGCGTACCACCCGTACCTGGACTTCATCAA
      R  P  G  L  L  L  T  V  A  V  G  A  G  I  D  K  I  R  V  T  D  P  A  A  Y  H  P  Y  L  D  F  I  N
                                                   BamHI
1901 CGTGATGACCTACGACTTCCACGGTGCGTGGGATCCGCAGACCAACCATCACTCGGCGCTGTTCGACTCCCCGGCCGACCCGTCCACCGGCGACCAGAAG
      V  M  T  Y  D  F  H  G  A  W  D  P  Q  T  N  H  H  S  A  L  F  D  S  P  A  D  P  S  T  G  D  Q  K

2001 CTCTACAACAGCAACGATGCGATGGAGGCGTTCCTGAGCCGTGGCGTGCCGGCGTCCAAGTTGAACCTGGGCATCGGCTACTACGGGCGCGGCTGGACCG
      L  Y  N  S  N  D  A  M  E  A  F  L  S  R  G  V  P  A  S  K  L  N  L  G  I  G  Y  Y  G  R  G  W  T  G

2101 GCGTGGCCAGTGGCAACAATGGCCTGTACAAGAGCGCCGGCGGCGCGGCACCGGGAACGTATGAAGCCGGCATCGAAGACTGGAAGGTGCTCAAGAACCT
      V  A  S  G  N  N  G  L  Y  K  S  A  G  G  A  A  P  G  T  Y  E  A  G  I  E  D  W  K  V  L  K  N  L

2201 GAACTGGCCGGTCTACACCGACACCGTCGCCAAGGCCACGTGGATCTCCAACGGCACCACCTTCTGGAGCGTGGATACCCCGGCGATGGTCACCGAGAAG
      N  W  P  V  Y  T  D  T  V  A  K  A  T  W  I  S  N  G  T  T  F  W  S  V  D  T  P  A  M  V  T  E  K

2301 ATGGGCTACGTGAAGGCCCAGGGACTGGGCGGCGCGTTCTTCTGGGAGTTCAGCGGCGATGACCCGCAGGGCACCCTGACCAAGGCCATCAGTGACGGGT
      M  G  Y  V  K  A  Q  G  L  G  G  A  F  F  W  E  F  S  G  D  D  P  Q  G  T  L  T  K  A  I  S  D  G  L

2401 TGAATTGATCTGAAACGGTGACGTGCAGCTGGGCAGAGCCCGGCTCTACCCACAAAAAAACGCCCCGGCACTGCCGGGGCGTTCTGGTTTCAGCGGCTGC
      N  .                                                                KpnI
2501 CGCCGGCCGTGATGCGCTCCAGCGCGGCCTTCAGCTGTGCCGGCGGCACGTAGCCGCCCAGCTGGGTGCCATCGGCGGCGAAGATCGCCGGGGTACCGTT
2601 CACGCCCATCTGCTGGCCCAGCGTGTACTGCATGGCCACCGGATTGGTGCAGTTTTTCGGCGCCACCGGCTGACCGGTCTTGGCCGCGGTGAGGGCCTGC
2701 TTGCGATCGGCCGCGCACCACACCGAAATCATGTCGGTGTAATCCTGGCTACCCAGCCCCATGCGCGGGAACGCGAGGTATTCCACGGTGATGCCGTTGC
        SacI
2801 GGTTGAGCTC
```

CHITINASE GENE FROM STENOTROPHOMONAS MALTOPHILIA

This application claims priority to U.S. No. 60/098,036, filed Aug. 27, 1998, the entirety of which is incorporated by reference herein.

FIELD OF THE INVENTION

This invention relates to the fields of agricultural microbiology and plant disease control. In particular, this invention provides a novel gene from *Stenotrophomonas maltophilia,* which encodes a chitinolytic enzyme useful for biocontrol of plant pathogenic fungi.

BACKGROUND OF THE INVENTION

Various scientific articles are referred to in brackets throughout the specification. These articles are incorporated by reference herein to describe the state of the art to which this invention pertains.

The use of chemical pesticides remains one of the most effective methods for control of plant diseases. However, concerns for health and environmental safety have increased pressure to reduce the use of chemicals in agriculture. Biological control using beneficial microbes is one alternative to chemicals that have yet to be fully investigated for plant disease control. However, in order for biocontrol to achieve full acceptance as disease control method, inconsistent performance of biocontrol agents in field conditions must be overcome. A major factor that contributes to inconsistent performance is the lack of efficient expression of biocontrol traits at the appropriate times and sites in the biosphere.

Bacteria that function in fungal pathogen antagonism by proposed lytic activity are described in the literature, dating as early as the 1960s. Investigative studies on the mechanisms by which these and similar strains function focus largely on the characterization of degradative enzymes. However, there are only limited studies that focus on the role of chitinases in biocontrol activity of lytic bacteria.

*Stenotrophomonas maltophilia* represents a rhizosphere bacterium of potential agronomic importance. *Stenotrophomonas maltophilia* strain 34S1 (Sm34S1) is capable of controlling summer patch disease of Kentucky bluegrass (*Poa pratensis*) caused by the root infecting fungus, *Magnaporthe poae* (Kobayashi et al., 1995, Soil Biol. Biochem. 27:1479–1487). The bacterium expresses several traits likely to contribute to biocontrol activity, including the production of several extracellular enzymes capable of degrading fungal cell wall components, including chitinase, protease and lipase (Kobayashi et al, 1995, supra; O'Brien and Davis, 1982, J. Clin. Microbiol. 16:417–421; Nord, et al., 1975, Med. Microbiol. Immunol. 161:79–87).

Chitinases digest chitin, the predominant polysaccharide in fungal cell walls. Chitin is an unbranched polymer of β-1,4-linked N-acetyl-D-glucosamine. Chitin is enzymatically degraded to N-acetylglucosamine by two distinct enzymes: an endochitinase [poly (1,4-N-acetyl-b-D-glucosaminidase; EC 3.2.1.14], which liberates mostly dimers and a chitobiase (N-acetyl-b-glucosaminidase; EC 3.2.1.30), which-reduces dimers to monomers for metabolic utilization. Characterized bacterial chitinases are endochitinases, and have been shown to rupture hyphal tips as well as inhibit spore germination (Inbar and Chet, 1991, Soil Biol. Biochem. 23:973–978; Lim, et al., 1991, Environ. Microbiol. 57:510–516).

Bacterial chitinases, as well as the genes that encode them and the bacterial strains that harbor them (either native strains or genetically engineered strains) are useful tools for biological control of fungal plant pathogens. Such tools could be used to minimize a fungal plant disease without the use, or with reduced use, of ecologically detrimental fungicides. Accordingly, it is of agronomic, economic and ecological importance to provide isolated genes encoding such chitinases, as well as the chitinases produced from such genes and bacterial strains that express the genes.

SUMMARY OF THE INVENTION

According to one aspect of the present invention, an isolated nucleic acid from Stenotrophomonas is provided. This isolated nucleic acid confers to bacteria in which it exists naturally, or into which it is transformed, the ability to delay the onset of symptoms of fungal infection in plants. The nucleic acid molecule is preferably isolated from *Stenotrophomonas maltophilia.* The isolated nucleic acid molecule described above encodes a chitinase. In a preferred embodiment, the isolated nucleic acid comprises the chiA gene from *S. maltophilia* strain 34S1, and in a most preferred embodiment, the isolated nucleic acid comprises part or all of SEQ ID NO:1.

According to another aspect of the invention, a biologically pure culture of Stenotrophomonas is provided that has the chiA gene in its genome. In a preferred embodiment, the culture is *S. maltophilia,* and in a most preferred embodiment, is strain 34S1.

According to another aspect of the invention, an isolated polypeptide is provided that is produced by expression of at least 30 consecutive nucleic acids of the aforementioned Stenotrophomonas isolated nucleic acid molecules. In a preferred embodiment, the polypeptide has an amino acid sequence comprising part or all of SEQ ID NO:2. Also included in this aspect are antibodies immunologically specific to this isolated polypeptide.

According to another aspect of the invention, an isolated nucleic acid molecule is provided that is at least 70% identical to SEQ ID NO:1 or ORFI of SEQ ID NO:1, a sequence encoding an amino acid sequence at least 60% similar to SEQ ID NO:2, and a nucleic acid molecule that hybridizes to SEQ ID NO:1 at moderate stringency.

According to another aspect of the invention, various recombinant DNA molecules are provided comprising variants of SEQ ID NO:1 and encoding variants of SEQ ID NO:2. These recombinant molecules include an expression cassette, a cloning vector and an Agrobacterium binary vector.

According to another aspect of the invention is a cell that has been transformed with a nucleic acid that is a variant of SEQ ID NO:1 or encodes a variant of SEQ ID NO:2. In a preferred embodiment, the cell transformed is a bacterial, yeast or plant cell. A more preferred embodiment is a biologically pure culture of this cell. Particularly preferred embodiments are a transgenic plant regenerated from the transformed plant cell, a seed from the plant and a plant from the seed.

According to another aspect of the invention, a method for protecting plants from fungal infection is provided. This method comprises introducing the chiA polypeptide into the environment of the plant. In a preferred embodiment, the chiA polypeptide is added as an isolated polypeptide. In another preferred embodiment, the chiA gene is expressed in an organism in the environment of the plant. In a more preferred embodiment, the organism is a transgenic microorganism, a transgenic plant, a transgenic fungus or a strain of *Stenotrophomonas maltophilia.* In another preferred embodiments, the organism is introduced into the soil around the plant or topically applied to the leaves of the plant.

According to another aspect of the invention, the transcription regulatory region of the *Stenotrophomonas maltophilia* chiA gene is provided. In a preferred embodiment, this regulatory region is disposed between nucleotides 1 and 306 of SEQ ID NO:1.

Other features and advantages of the present invention will be better understood by reference to the drawings, detailed description and examples that follow.

BRIEF DESCRIPTION OF THE DRAWINGS

FIG. 1. Nucleotide sequence of the 2.8 kb XhoI-SacI fragment containing chitinase activity from *Stenotrophomonas maltophilia* 34S1. The predicted translation product for the chitinase gene, depicted in single letter amino acid code, is located below the nucleotide sequence, and the position of relevant restriction enzyme sites are indicated above the sequence. A putative ribosome binding site preceding the predicted translational start is shown in bold nucleotide sequence. An inverted repeat suggestive of a transcriptional stop is underlined and shown in bold nucleotide sequence. Amino acid sequence resembling a signal peptide is underlined, with bold lettering representing classic principle features. An arrow above the sequence indicates the predicted cleavage site.

FIG. 3. Summer patch disease symptom development in Kentucky bluegrass var. Baron treated with *Stenotrophomonas maltophilia* strains. The graph represents mean values for disease from one of five experimental trials (trial II). Disease was rated over a 29 day period beginning 1 week (day 1) after plants were moved to disease conducive conditions. Lines through squares represent untreated control plants; diamonds represent plants treated with chiA mutant C5; circles represent plants treated with Sm34S1; triangle represents uninoculated, healthy control plants. The same letters next to data points for each observation date indicate no significant differences according to a protected least significant difference test (P=0.05).

DETAILED DESCRIPTION OF THE INVENTION

I. Definitions

Various terms relating to the biological molecules of the present invention are used hereinabove and also throughout the specification and claims. The terms "substantially the same," "percent similarity" and "percent identity" are defined in detail below.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eucaryote. An "isolated nucleic acid molecule" may also comprise a cDNA molecule.

With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

Nucleic acid sequences and amino acid sequences can be compared using computer programs that align the similar sequences of the nucleic or amino acids thus define the differences. For purposes of this invention, the Clustal program in the GCG Wisconsin Package version 9.1, available from the Genetics Computer Group in Madison, Wis., and the default parameters used by that program are the parameters intended to be used herein to compare sequence identity and similarity.

For purposes of this invention, the term "substantially the same" refers to nucleic acid or amino acid sequences having sequence variation that do not materially affect the nature of the protein (i.e. its structure and/or biological activity). With particular reference to nucleic acid sequences, the term "substantially the same" is intended to refer to coding regions and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide that do not affect structure or function. The terms "percent identity" and "percent similarity" are also used herein in comparisons among amino acid sequences. These terms are intended to be defined as they are in the UWGCG sequence analysis program (Devereaux et al., Nucl. Acids Res. 12: 387–397, 1984), available from the University of Wisconsin.

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "substantially pure" refers to a preparation comprising at least 50–60% by weight the compound of interest (e.g., nucleic acid, oligonucleotide, protein, etc.). More preferably, the preparation comprises at least 75% by weight, and most preferably 90–99% by weight, the compound of interest. Purity is measured by methods appropriate for the compound of interest (e.g. chromatographic methods, agarose or polyacrylamide gel electrophoresis, HPLC analysis, and the like).

With respect to antibodies of the invention, the term "immunologically specific" refers to antibodies that bind to one or more epitopes of a protein of interest, but which do not substantially recognize and bind other molecules in a sample containing a mixed population of biological molecules.

With respect to oligonucleotides, the term "specifically hybridizing" refers to the association between two single-stranded nucleotide molecules of sufficiently complementary sequence to permit such hybridization under predetermined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "expression cassette" refers to a genetic module comprising a gene with the regulatory regions necessary for its expression in host cell.

The term "promoter region" refers to the 5' regulatory regions of a gene, including promoters per se, as well as translational control regions, enhancer elements and other regulatory sequence found in the region of a gene 5' to the translation start site.

The term "vector" refers to a small carrier DNA molecule into which a DNA sequence can be inserted for introduction into a host cell where it will be replicated. An "expression vector" is a specialized vector that contains a gene with the necessary regulatory regions needed for expression in a host cell.

The term "binary vector" refers to vector which carries a modified T-region from the Ti plasmid usually comprising selectable markers for plant transformation between the two boarder regions. A gene of interest can also be placed between these two boarder regions for transfer into a plant cell genome with the assistance of a helper plasmid and the bacterium *Agrobacterium tumefaciens*.

The term "selectable marker gene" refers to a gene product that when expressed confers a selectable phenotype, such as antibiotic resistance, on a transformed cell or plant.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector.

The term "DNA construct" refers to genetic sequence used to transform bacteria or plants. These constructs may be administered to an organism in a viral or plasmid vector. For plant transformation, other methods of delivery such as Agrobacterium T-DNA mediated transformation and transformation using the biolistic process are also contemplated to be within the scope of the present invention. The transforming DNA may be prepared according to standard protocols such as those set forth in "Current Protocols in Molecular Biology", eds. Frederick M. Ausubel et al., John Wiley & Sons, 1995. The term "transgene" is used to refer to the DNA construct within the transformed cell or plant.

II. Description of chiA, its Encoded Polypeptide, and Method of using chiA for Disease Resistance In accordance with the present invention, a novel chitinase gene, chiA, has been isolated from the bacteria, *Stenotrophomonas maltophilia*. This gene was isolated due to the insight to use *Burkholderia cepacia* M53 as a heterologous expression system. The chiA gene has a novel active domain complement that suggests it has unique functional properties. The chiA gene and the strain of bacteria it was isolated from, *S. maltophilia* 34S1, have been found to be very effective in slowing a soil-borne fungal infection in plants.

A genomic clone of chiA from *Stenotrophomonas maltophilia* is described in detail herein and its nucleotide structure is set forth herein as SEQ ID NO:1. Briefly, the chiA gene was isolated by screening a *S. maltophilia* cosmid genomic library for chitinase activity in *Burkholderia cepacia*. Two genomic cosmids were isolated with this approach, pXM12H2 and pXM7B5. Restriction digests and southern blots showed the two clones had a region of homologous overlap. Cosmid pXM7B5 was selected for further characterization.

The nucleotide sequence of the 2.8 kb DNA fragment in cosmid pXM7B5 contained two open reading frames. The larger open reading frame (ORFI) of 2100 bases completely encompasses the smaller open reading frame (ORFII) of 1848 bases. Open reading frame 1 contains a predicted start ATG codon that is preceded by a purine-rich sequence resembling a ribosome binding site. A 700 amino acid protein is predicted from ORFI with a molecular weight of 72.4 kDa. The first 41 residues of the predicted translation product of ORFI resembles a signal peptide. If the signal peptide is cleaved at the predicted site, the resulting peptide is predicted to be 68 kDa. The second open reading frame lacks a detectable translation start codon preceded by sequences resembling a ribosome binding site. Truncated clones of the 2.8 kB DNA fragment verify that chitinase activity is associated with ORFI. No sequences were found for ORFII.

Significant sequence identities were detected between ORFI and chitinases in the GenBank data base, using the CLUSTAL method of comparison. The highest degrees of sequence similarities were found to genes derived from organisms with equivalently high %G+C content.

The chiA predicted protein contains a catalytic domain and two fibronectin binding domains. It does not have the cellulose/chitin binding domain found in most chitinases, and its catalytic domain is in the C-terminal half of protein. In many, but not all, chitinases, the catalytic domain is in the N-terminal portion of the protein.

SDS-page and activity analysis of the chitinase expressed and secreted from *S. maltophilia* strain 34S1 reveals a polypeptide of an approximate size of 47.5 kDa, which is significantly smaller than the size predicted from the deduced amino acid sequence of ORFI as well as from the size of the protein expressed and secreted in *Burkholderia cepacia*. This unexpected difference in the respective sizes of the proteins may be due to an additional processing step that occurs naturally in *S. maltophilia*, but not in a non-native host such as *B. cepacia*, resulting in a smaller mature polypeptide. Alternatively, it may be due to a post-translational modification that results in anomalous migration in SDS-PAGE.

A strain of *S. maltophilia* with a defective chiA gene was generated by site-directed marker exchange mutagenesis. Wild-type *S. maltophilia* was found to secrete a 47.5 kDa protein into the culture medium that had chitinase activity. The mutated *S. maltophilia* strain had neither the chitinase activity nor the 47.5 kDa protein in its culture medium.

The chiA mutant and the wild type *S. maltophilia* strains were compared to controls (no bacteria present) for their ability to slow the progress of summer patch disease in Kentucky bluegrass. Soil inoculations with the wild type *S. maltophilia* were statistically better able than the chiA mutant strain to slow the onset of summer patch disease in Kentucky blue grass. Both the chiA mutant strain and the wild type strain of *S. maltophilia* showed significant slowing of disease onset as compared to null controls.

Although the chiA genomic clone from *S. maltophilia* is described and exemplified herein, this invention is intended to encompass nucleic acid sequences and proteins from other organisms, including bacteria, fungi, plants, yeast, insects and mammals, that are sufficiently similar to be used instead of the Stenotrophomonas chiA nucleic acid and proteins for the purposes described below. These include, but are not limited to, allelic variants and natural mutants of SEQ ID NO:1, which are likely to be found in different species of bacteria or varieties of Stenotrophomonas. Because such variants are expected to possess certain differences in nucleotide and amino acid sequence, this invention provides an isolated chiA nucleic acid molecule having at least about 70% (preferably 80% and more preferably over 90%) sequence identity in the coding regions with the nucleotide sequence set forth as SEQ ID NO:1 (and, most preferably, specifically comprising the coding region of SEQ ID NO:1). The length of the isolated nucleic acid of the invention may vary in length and is 15 nucleotides, 30 nucleotides and 60 nucleotides in preferred, more preferred and most preferred embodiments. The chiA nucleic acid of the invention may hybridize to SEQ ID NO:1 under conditions of moderate stringency, high stringency and very high stringency in preferred, more preferred and most preferred embodiments, respectively. This invention also provides isolated polypeptide products of the open reading frames of SEQ ID NO:1, having at least about 60% (preferably 75% or 90% or greater) sequence similarity with the amino acid sequences of SEQ ID NO:2.

Because of the natural sequence variation likely to exist among chiA genes, one skilled in the art would expect to find up to about 30–40% nucleotide sequence variation, while still maintaining the unique properties of the chiA gene and encoded polypeptide of the present invention. Such an expectation is due in part to the degeneracy of the genetic code, as well as to the known evolutionary success of conservative amino acid sequence variations, which do not appreciably alter the nature of the encoded protein. Accordingly, such variants are considered substantially the same as one another and are included within the scope of the present invention.

Provided in accordance with the invention are organisms that express the chiA chitinase gene of the invention, both naturally and through transgenes. In accordance with the invention it has been determined that the expression of the chiA gene in *Stenotrophomonas maltophilia* confers to this bacteria its fungicidal properties. As described in the Example, the mutation of the chiA gene was found to eliminate the fungicidal properties of that bacteria. In a preferred embodiment, the bacteria express an endogenous chiA gene, and in a most preferred embodiment, the bacteria is *Stenotrophomonas maltophilia*. It is contemplated that other closely related bacteria will also express endogenous genes substantially the same as the chiA gene of the invention, and these related bacteria are also considered to be part of the invention.

Bacteria can be bio-engineered to over-express chiA in order to deter pathogenic fungi. It is particularly advantageous to select bacteria that are natural soil-borne bacteria of the plant species in which fungal infection is a problem. For instance, another soil-borne chitinolytic bacterium, such as *Lytobacter kobii*, may be engineered to overexpress the chiA gene. Alternatively, a non-chitinolytic soil-borne bacterium may be made chitinolytic by transforming it with a chiA gene. In a preferred embodiment, a plant growth-promoting bacterium, such as Rhizobium or Azospirillum, is engineered to express the chiA gene. In another preferred embodiment, the chiA transgene comprises a secretion signal.

Transgenic plants that over-express chiA also provided with the present invention. It is contemplated that these plants will have increased resistance to fungal infection. In a preferred embodiment, chiA is secreted into the intercellular spaces of leaf tissue and other infectable tissues. In another preferred embodiment, chiA is expressed in root tissue and secreted into the soil. Plant species of interest include, but are not limited to, turfgrasses such as Kentucky bluegrass, perennial ryegrass, hard fescue, Chewings fescue, strong creeping fescue and colonial bentgrass, as well as any other plant species for which enhanced resistance to fungal plant pathogens is desired (e.g., vegetable crops such as tomatoes, cucumbers and eggplants; grain crops such as corn, wheat and rice; legumes and fruit trees, among others).

Also provided with the invention is a method for protecting plants from pathogenic fungi. The basis of this method is the introduction of the chiA chitinase of the invention into the environment of the plant. While in the most preferred embodiment chiA is introduced into the rhizosphere of the plant, this method also encompasses embodiments where chiA is introduced to the environment of the plant in general. The introduction of chiA can be simply introducing the protein, but in preferred embodiments, chiA is the product of the expression of the chiA gene in the environment of the plant. In one preferred embodiment, the chiA gene is expressed by a bacteria in which it is endogenous, such as *Stenotrophomonas maltophilia*. In another preferred embodiment, a chiA transgene is expressed by a bacteria, plant or fungi. In a more preferred embodiment, the chiA transgene is expressed by a soil-borne bacteria. In most preferred embodiments, the chiA transgene is expressed by *Lytobacter mycophilus*, Rhizobium or Azospirillum.

The following description sets forth the general procedures involved in practicing the present invention. To the extent that specific materials are mentioned, it is merely for purposes of illustration and is not intended to limit the invention. Unless otherwise specified, general cloning procedures, such as those set forth in Sambrook et al., *Molecular Cloning*, Cold Spring Harbor Laboratory (1989) (hereinafter "Sambrook et al.") or Ausubel et al. (eds) *Current Protocols in Molecular Biology*, John Wiley & Sons (1999) (hereinafter "Ausubel et al.") are used.

A. Preparation of chiA Nucleic Acid Molecules, Encoded Polypeptides and Antibodies Specific for the Polypepides 1. Nucleic Acid Molecules ChiA nucleic acid molecules of the invention may be prepared by two general methods: (1) they may be synthesized from appropriate nucleotide triphosphates, or (2) they may be isolated from biological sources. Both methods utilize protocols well known in the art.

The availability of nucleotide sequence information, such as the genomic DNA fragment having SEQ ID NO:1, enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a long double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire long double-stranded molecule. A synthetic DNA molecule so constructed may then be cloned and amplified in an appropriate vector.

ChiA genes also may be isolated from appropriate biological sources using methods known in the art. In the exemplary embodiment of the invention, the S. maltophilia chiA clone was isolated from a genomic cosmid library of S. maltophilia. ChiA genes can likewise be isolated from other organisms, such as other strains or species of Stenotrophomonas, using methods well known to those skilled in the art. In an alternative embodiment, cDNA clones of the genomic chiA locus may be isolated. A preferred means for isolating chiA cDNAs is PCR amplification using cDNA templates and chiA coding sequence specific primers.

In accordance with the present invention, nucleic acids having the appropriate level sequence homology with part or all the coding regions of SEQ ID NO:1 may be identified by using hybridization and washing conditions of appropriate stringency. For example, hybridizations may be performed, according to the method of Sambrook et al., using a hybridization solution comprising: 5×SSC, 5×Denhardt's reagent, 1.0% SDS, 100 µg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 2×SSC and 0.1% SDS; (4) 2 hours at 45–55° C. in 2×SSC and 0.1% SDS, changing the solution every 30 minutes.

One common formula for calculating the stringency conditions required to achieve hybridization between nucleic acid molecules of a specified sequence homology (Sambrook et al., 1989):

$$T_m=81.5° C.+16.6Log[Na+]+0.41(\%G{\leftrightarrows}C)-0.63(\% \text{ formamide})-600/\#bp \text{ in duplex}$$

As an illustration of the above formula, using [N+]=[0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C. Such a sequence would be considered substantially homologous to the sequences of the present invention.

The Stringency of the hybridization and wash depend primarily on the salt concentration and temperature of the solutions. In general, to maximize the rate of annealing of the probe with its target, the hybridization is usually carried out at salt and temperature conditions that are 20–25° C. below the calculated $T_m$ of the hybrid. Wash conditions should be as stringent as possible for the degree of identity of the probe for the target. In general, wash conditions, are selected to be approximately 12–20° C. below the $T_m$ of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1×SSC and 0.5% SDS at 65° C. for 15 minutes.

Nucleic acids of the present invention may be maintained as DNA in any convenient cloning vector. In a preferred embodiment, clones are maintained in plasmid pRK415 (Keen, et al., 1988, Gene 70:191–197), which is a broad host range plasmid capable of being mobilized and replicated in a variety of heterologous bacterial hosts. Other suitable cloning/expression vectors include, but are not limited to, such as pGEM (Promega Biotech, Madison, Wis.) or pBluescript (Stratagene, La Jolla, Calif.), either of which is propagated in a suitable E. coli host cell.

ChiA nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of the DNA having SEQ ID NO:1. Such oligonucleotides are useful as probes for detecting chiA genes or mRNA in test samples, e.g. by PCR amplification, or for the positive or negative regulation of expression of chiA genes at or before translation of the mRNA into proteins.

The chiA promoter and other expression regulatory sequences for chiA are also expected to be useful in connection with the present invention. SEQ ID NO:1 shows about 300 bp of sequence upstream from the beginning of the coding region, which contains such expression regulatory sequences.

2. Proteins

Polypeptides encoded by chiA nucleic acids of the invention may be prepared in a variety of ways, according to known methods. If produced in situ the polypeptides may be purified from appropriate sources, e.g., bacterial cultures. In a preferred embodiment, the polypeptides are purified from the culture media in which the bacterial cells are growing.

Alternatively, the availability of nucleic acid molecules encoding the polypeptides enables production of the proteins using in vitro expression methods known in the art. For example, a cDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech (Madison, Wis.) or BRL (Rockville, Md.).

Larger quantities of chiA-encoded polypeptide may be produced by expression in a suitable procaryotic or eucaryotic system. For example, part or all of a DNA molecule, such as the coding portion of SEQ ID NO:1, may be inserted into a plasmid vector adapted for expression in a bacterial cell (such as E. coli) or a yeast cell (such as Saccharomyces cerevisiae), or into a baculovirus vector for expression in an insect cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences. In a preferred embodiment, the expression vector would be pRK415 and the host cell would be Burkholderia cepacia M53.

The chiA polypeptide produced by gene expression in a recombinant procaryotic or eucaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/ secretion vectors are not used, an alternative approach involves purifying the recombinant protein by affinity separation, such as by immunological interaction with antibodies that bind specifically to the recombinant protein. Such methods are commonly used by skilled practitioners.

The chiA-encoded polypeptides of the invention, prepared by the aforementioned methods, may be analyzed according to standard procedures. Chitinase activity assays may be carried out in liquid reaction media, using one of numerous assay systems known in the art. In a preferred embodiment, proteins with chitinase activity are detected in native gels impregnated with 0.1 mM 4-methylumbelliferyl b-D-NN'-diacetylchitobioside [4-MU-(GlcNAc)$_2$] or 4-methylumbelliferyl b-D-NN'-triacetylchitobioside [4-MU-(GlcNAc)$_3$] (Sigma), as described in the Example.

The present invention also provides antibodies capable of immuno-specifically binding to polypeptides of the invention. Polyclonal or monoclonal antibodies directed toward the polypeptide encoded by chiA may be prepared according to standard methods. Monoclonal antibodies may be prepared according to general methods of Köhler and Milstein (1992, Biotechnology 24:524–526), following standard protocols. In a preferred embodiment, antibodies are prepared, which react immuno-specifically with various epitopes of the chiA-encoded polypeptides.

3. Transgenic Organisms

Bacteria expressing the chiA gene can be created by methods well known to those skilled in the art of bacterial genetics. The expression of the chiA gene can be accomplished by operably linking promoters with specific expression characteristics to the chiA coding sequence. Suitable strong constitutive promoters include, but are not limited to, the lac, trp or tac promoters. Inducible bacterial promoters are also contemplated for use in the present invention. In a preferred embodiment, the chiA native promoter is used. In another preferred embodiment, a bacterial promoter that is induced in bacteria when fungi are present is used.

Transgenic plants expressing the chiA gene can be generated using standard plant transformation methods known to those skilled in the art. These include, but are not limited to, Agrobacterium vectors, PEG treatment of protoplasts, biolistic DNA delivery, UV laser microbeam, gemini virus vectors, calcium phosphate treatment of protoplasts, electroporation of isolated protoplasts, agitation of cell suspensions with microbeads coated with the transforming DNA, direct DNA uptake, liposome-mediated DNA uptake, and the like. Such methods have been published in the art. See, e.g., *Methods for Plant Molecular Biology* (Weissbach & Weissbach, eds., 1988); *Methods in Plant Molecular Biology* (Schuler & Zielinski, eds., 1989); *Plant Molecular Biology Manual* (Gelvin, Schilperoort, Verma, eds., 1993); and *Methods in Plant Molecular Biology—A Laboratory Manual* (Maliga, Klessig, Cashmore, Gruissem & Varner, eds., 1994).

The method of transformation depends upon the plant to be transformed. Transformation and regeneration methods are particularly well established for many plants of agronomic importance. The biolistic DNA delivery method is useful for nuclear transformation. Agrobacterium vectors are also used to advantage for efficient transformation of plant nuclei (Bevan, 1982, Ann. Rev. Genet 16:357–384; Rogers et al., 1986, Methods in Enzyl. 118:627–641). The gene is introduced into plant nuclei in Agrobacterium binary vectors. Such vectors include, but are not limited to, BIN19 (Bevan, 1984, Nuc. Acid Res. 12:8711–8721) and derivatives thereof, the pBI vector series (Jefferson et al., 1987, EMBO J 6:3901–3907), and binary vectors pGA482 and pGA492 (An, 1986) among others (for review, see An, 1995, Methods Mol Biol 44:47–58). Both of these transformation methods and their variations will be well know to those skilled in the art.

The chiA gene coding sequence may be operably linked to specialized promoters to give general or tissue-specific expression patterns in plants. Strong constitutive promoters include, but are not limited to, the Cauliflower Mosaic Virus (CaMV) 35S promoter, the T-DNA mannopine synthetase promoter or the figwort mosaic virus 35S promoter. If root specific expression is desired, the promoters for genes encoding glutamine synthetase can be used (Tingey et al., 1987, EMBO J. 6:1–9; Edwards et al., 1990, Proc. Natl. Acad. Sci. USA 87:3459–3463). Transgenic plants expressing the chiA gene under an inducible promoter (either its own promoter or a heterologous promoter) are also contemplated to be within the scope of the present invention. Inducible plant promoters include the tetracycline repressor/operator controlled promoter. Transgenic bacteria may also express chiA under an inducible promoter that is endogenous to bacteria.

It should be recognized that the amount of expression, as well as the tissue specificity of expression of the chiA gene in transformed cells can vary depending on the position of their insertion into the nuclear genome. Such position effects are well known in the art. For this reason, several nuclear transformants should be regenerated and tested for expression of the transgene.

B. Uses of ChiA Nucleic Acids, Encoded Proteins and Antibodies

1. ChiA Nucleic Acids

ChiA nucleic acids may be used for a variety of purposes in accordance with the present invention. The DNA, RNA, or fragments thereof may be used as probes to detect the presence of and/or expression of chiA genes. Methods in which chiA nucleic acids may be utilized as probes for such assays include, but are not limited to: (1) in situ hybridization; (2) Southern hybridization (3) northern hybridization; and (4) assorted amplification reactions such as polymerase chain reactions (PCR).

The chiA nucleic acids of the invention may also be utilized, and have been utilized by the inventor, as probes to identify related genes from other species, including but not limited to, bacteria, fungi, plants, yeast, insects and mammals, including humans. As is well known in the art and described above, hybridization stringencies may be adjusted to allow hybridization of nucleic acid probes with complementary sequences of varying degrees of homology. Thus, chiA nucleic acids may be used to advantage to identify and characterize other genes of varying degrees of relation to the exemplary coding sequence of SEQ ID NO:1, thereby enabling further characterization of this family of genes.

In the Example, chiA gene function in *S. maltophilia* was found to be useful in delaying the onset of summer patch disease in Kentucky bluegrass. Without intending to be bound by any particular function of the chiA gene, it appears that the chitinase secreted by *S. maltophilia* into the soil digests fungal cell walls and kills the soil-borne plant pathogenic fungi *Magnaporthe poae*. Strains of *S. maltophilia* that over-express chiA may therefore be very useful and delay the onset of summer patch disease even longer. The chiA gene and the *S. maltophilia* strain 34S1 are expected to have similar efficacies to other fungi-originated diseases, including but not limited to, take-all patch, spring dead spot and necrotic ring spot.

ChiA-expressing bacteria may also be applied topically to plant foliage or through soil inoculation. Bacteria overexpressing the chiA gene may also be useful in controlling fungal growth in other applications, such as biofilms.

2. ChiA Proteins and Antibodies

Purified chiA-encoded proteins, or fragments thereof, may be used to produce polyclonal or monoclonal antibodies which also may serve as sensitive detection reagents for the presence and accumulation of chiA-encoded protein in cultured cells or tissues and in intact organisms. Recombinant techniques enable expression of fusion proteins containing part or all of the chiA-encoded protein. The full length protein or fragments of the protein may be used to advantage to generate an array of monoclonal or polyclonal antibodies specific for various epitopes of the protein, thereby providing even greater sensitivity for detection of the protein in cells or tissue.

ChiA gene products also may be useful as an externally applied biological control agent. For instance, preparations of the purified protein may be sprayed on plant parts or inoculated into soil, to introduce chitinolytic activity and thereby slow or prevent infection of plants by fungal plant pathogens.

Polyclonal or monoclonal antibodies immunologically specific for chiA-encoded proteins may be used in a variety of assays designed to detect and quantitate the protein. Such assays include, but are not limited to: (1) flow cytometric analysis; (2) immunochemical localization in cultured cells or tissues; and (3) immunoblot analysis (e.g., dot blot, Western blot) of extracts from various cells and tissues.

Polyclonal or monoclonal antibodies that immunospecifically interact with the polypeptide encoded by chiA can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules. Monoclonal antibodies made to unique regions of the chiA protein may also be used to identify *S. maltophilia* in mixed populations of bacteria.

The following example is provided to describe the invention in greater detail. It is intended to illustrate, not to limit, the invention.

Example 1

Cloning and Characterization of the Chitinase Gene from *S. maltophilia*

Materials and Methods

Bacterial and fungal strains, vectors and media. Bacterial strains, plasmids and phage used in this study are listed in Table 1. All strains were grown and maintained on LB agar (Difco). Strains containing plasmids were maintained on LB agar supplemented with appropriate antibiotics at the following levels unless otherwise noted: tetracycline (Tc) 12.5 μg/ml; kanamycin (Km) 50 μg/ml; ampicillin (Ap) 50 μg/ml; rifampicin (Rif) 100 μg/ml. *Magnaporthe poae* strain 73-15 (ATCC culture 64411) was maintained on potato dextrose agar (PDA) (Difco).

Construction of *S. maltophilia* genomic library and screening for chitinase activity. Total genomic DNA of *S. maltophilia* 34S1 was isolated using the sodium dodecyl sulfate (SDS) lysis procedure previously described (Staskawicz, et al., 1984, Proc. Natl. Acad. Sci. USA 81:6024–6028). DNA was purified twice on a cesium chloride gradient, and 60 μg of DNA was partially digested with Sau3A before size-fractionating on a 10–40% glycerol gradient centrifuged at 194,000 ×g for 33 h in a Beckman SW40 rotor. DNA fragments greater than 15 kb were collected and ligated to the BamHI site in pLAFR3, and packaged into lambda phage using Gigapak extracts (Stratagene). Packaged phage were used to infect *E. coli* HB101.

No positive clones for chitinase activity were detected when the entire genomic library was initially screened in *E. coli.* Therefore, the entire library was mobilized into *Burkholderia cepacia* M53, a strain that lacks chitinase activity, by triparental matings (Ditta, et al., 1985, Plasmid 13:149–153). Transconjugants were plated on M9 minimal salts (Sambrook, et al., 1989. *Molecular cloining: A laboratory manual,* 2nd ed. Cold Spring Harbor Laboratory Press, Cold Spring Harbor, N.Y.) in 0.7% agarose supplemented with 0.25% yeast extract (Difco), 2% colloidal chitin (Lingappa and Lockwood, 1961, Phytopathology 52:317–323) and 200 mg/ml Tc.

Molecular characterization and sequence analysis. Restriction digests, electrophoresis, ligations and Southern hybridizations were performed as described (Sambrook, et al., 1989, supra). Nucleotide sequence was determined by the dideoxy chain termination method (Sanger, et al., 1977, Proc. Natl. Acad. Sci. USA 74:5463–5467). Manual sequencing was performed by $^{35}$S-labeling using Sequenase (Version 2.0, US Biochemical). Automated sequencing was performed by fluorescence-labeling using Amplitaq FS (Applied Biosystems Inc.) run on an ABI model 373 automated sequencer. All nucleotide

TABLE 1

Strains, plasmids and transposons

| Strain/plasmid | Description | Source/ Reference |
|---|---|---|
| *Escherichia coli* | | |
| DH5α | | Gibco/BRL |
| HB101 | | Gibco/BRL |
| *Stenotrophomonas maltophilia* | | |
| 34S1 | Wild type strain, Rif$^r$ | Keen et al., 1988, Gene 70:191–197 |
| C5 | Marker exchange, chiA mutant of Sm34S1 | This study |
| *Burkholderia cepacia* | | |
| M53 | Wild type | Laboratory collection |
| Plasmids | | |
| pUC118 | | NEB |
| pRK415 | 10.4 kb broad host range vector; mob+; Tc$^r$; pUC19 polylinker | Keen et al., 1988, Gene 70:191–197 |
| pLAFR3 | Cosmid cloning vector; mob+; Tc$^r$ | Staskawicz et al., 1986, J. Bacteriol. 169:5789–5794 |
| pXM7B5 | Cosmid clone from 34S1 genomic library containing chitinase activity | This example |

TABLE 1-continued

Strains, plasmids and transposons

| Strain/plasmid | Description | Source/Reference |
|---|---|---|
| pXM12H2 | Cosmid clone from 34S1 genomic library containing chitinase activity | This example |
| pXMC131 | 2.8 kb XhoI-SacI fragment from pXM7B5 containing chitinase activity cloned into SalI and SacI sites in the polylinker of pUC118 | This example |
| pXMC431 | 2.8 kb XhoI-SacI fragment from pXM131 excised as a HindIII-EcoRI fragment cloned in pRK415 | This example |
| pXMC441 | 2.1 kb KpnI fragment cloned in pRK415 | This example |
| pXMC452 | 2.5 kb PstI-SacI fragment cloned in pRK415. | This example |
| pXMC333 | a 1.9 kb XhoI-BamHI fragment of the representing the 5' end of the chiA gene excised from pXM131 using the HindIII polylinker site and the BamHI site internal to the ORF, cloned into pLAFR3 | This example |
| pXM7B5::Tn5-1 | cosmid containing Tn5 in 0.2 kb KpnI fragment devoid of chitinase activity | This example |
| λ::Tn5 | | DeBruijn and Lupski, 1984, Gene 27:131–149 | sequences and trace plots were analyzed using the DNA analysis programs of DNAStar (Lasergene).

Transposon mutagenesis of cosmid clones contained in *E. coli* was performed using λ::Tn5 as described (De Bruijn, et al., 1984, Gene 27:131–149). A single cosmid containing Tn5 in the coding region of the chitinase gene was selected and used for site-directed mutagenesis using the method of Ruvkun and Ausubel (1981, Nature 289:85–88) as previously described (Lorang, et al., 1994, Molec. Plant Microbe Inter. 7:508–515).

Isolation and characterization of extracellular chitinase. To characterize extracellular enzymes in culture filtrates, all bacteria were grown in M9 salts broth supplemented with 0.25% yeast extract and 2% colloidal chitin. *S. maltophilia* transconjugants and *B. cepacia* transconjugants were grown in the medium supplemented with Tc at 100 μg/ml and 200 mg/ml, respectively. After 3 days growth at 30° C., cells were pelleted by centrifugation (10 min×7500 g), and culture filtrates were precipitated with 80% ammonium sulfate at room temperature for 60 min before centrifuging for 15 min (×16, 16,000 g). Pellets were resuspended in 1/1000 the original volume and dialyzed in 10 mM Tris pH 8.0.

SDS-polyacrylamide gel electrophoresis (PAGE) was run as previously described (Laemmli, 1970, Nature 227:680–685). Non-denaturing (native) gels consisted of a resolving gel of 10% acrylamide in 0.375 M Tris-Cl pH 6.8 with a stacking gel of 3.9% acrylamide in 0.125 M Tris-Cl pH 6.8. Chitinase activity was detected by UV light exposure of native gels impregnated with 0.1 mM 4-methylumbelliferyl b-D-NN'-diacetylchitobioside [4-MU-(GlcNAc)$_2$] or 4-methylumbelliferyl b-D-NN'-triacetylchitobioside [4-MU-(GlcNAc)$_3$] (Sigma). Gels were photographed with 400 ISO color slide film which was later converted to digital image for output.

Greenhouse/growth chamber experiments. Biocontrol assays for summer patch disease were conducted on Kentucky bluegrass var. Baron grown in a 4:1 mix of pasteurized sand/peat in 9 cm conical containers as previously described (Kobayashi et al., 1995, Soil Biol. Biochem. 27:1479–1487). Containers were inoculated with the fungal pathogen at a depth of 1.5 cm below the soil surface at the time that seeds were sown. Bacteria were prepared as treatments by pelleting cells from overnight cultures grown in LB and suspending in sterile H$_2$O to a concentration of 5×10$^8$ cfu/ml. 25 ml of the bacterial solution was applied to each container as a soil drench at 2 and 3 weeks after seeding. Plants were moved to the growth chamber, set at 30° C. and 70% humidity 500 μE light at 14 h, 4 weeks after seeding to induce disease. Plants were rated based on a visual assessment of the percentage of necrotic leaves within a container as described (Kobayashi and El-Barrad, 1996, Cur. Microbiol. 32:106–110). Each treatment was replicated 10 times within an experiment, and the experiment was repeated five times. All results were analyzed using the general linear models procedure of SAS (SAS Institute, Cary, N.C.).

*S. maltophilia* populations in the Kentucky bluegrass var. Baron rhizosphere were performed according to the procedure described (Kobayashi et al., 1995, Soil Biol. Biochem. 27:1479–1487). Populations were sampled 1, 4, 7, 10 and 14 days after application. All samples were dilution plated onto LB agar supplemented with Rif. Samples were replicated three or five times, depending on the experiment, and the experiment was repeated three times.

Nucleotide sequence accession number. The nucleotide sequence of chiA was deposited in the Genbank database under Accession No. AF014950.

Results

Cloning and characterization of the chitinase gene from *S. maltophilia*. Mobilization of the entire library into *B. cepacia* M53 resulted in the identification of two cosmids, pXM7B5 and pXM12H2, that caused bacterial colonies to clear colloidal chitin in agar within five days. Comparisons of restriction digest banding patterns indicated that the two cosmids shared a region of overlap, which was later confirmed to be homologous by Southern hybridizations. As a consequence, only cosmid pXM7B5 was selected for further characterization.

Chitinase activity from pXM7B5 was subcloned to a 2.8 kb XhoI-SacI fragment by first ligating into the SalI and SacI sites located in the polylinker of pUC118 to form plasmid pXMC131. This subclone was excised as a HindIII-EcoRI fragment using restriction sites located in the vector polylinker and ligated into the low copy number broad host range vector, pRK415 (Keen, et al., 1988. Gene 70:191–197). The resulting plasmid, pXMC431, was mobilized into *B. cepacia* M53 and found to express chitinase activity on colloidal chitin medium. Low level chitinase activity was detected when *E. coli* cells containing pXMC431 were plated on the chitin medium amended with IPTG, but only after a minimum of two weeks incubation at 30° C. In contrast, no chitinase activity was detected with *E. coli* cells containing the high copy plasmid pXMC131, which positioned the cloned fragment in the opposite direction of the vector lacZ promoter compared to pXMC431, even following chloroform lysis of cells.

Figure 1:
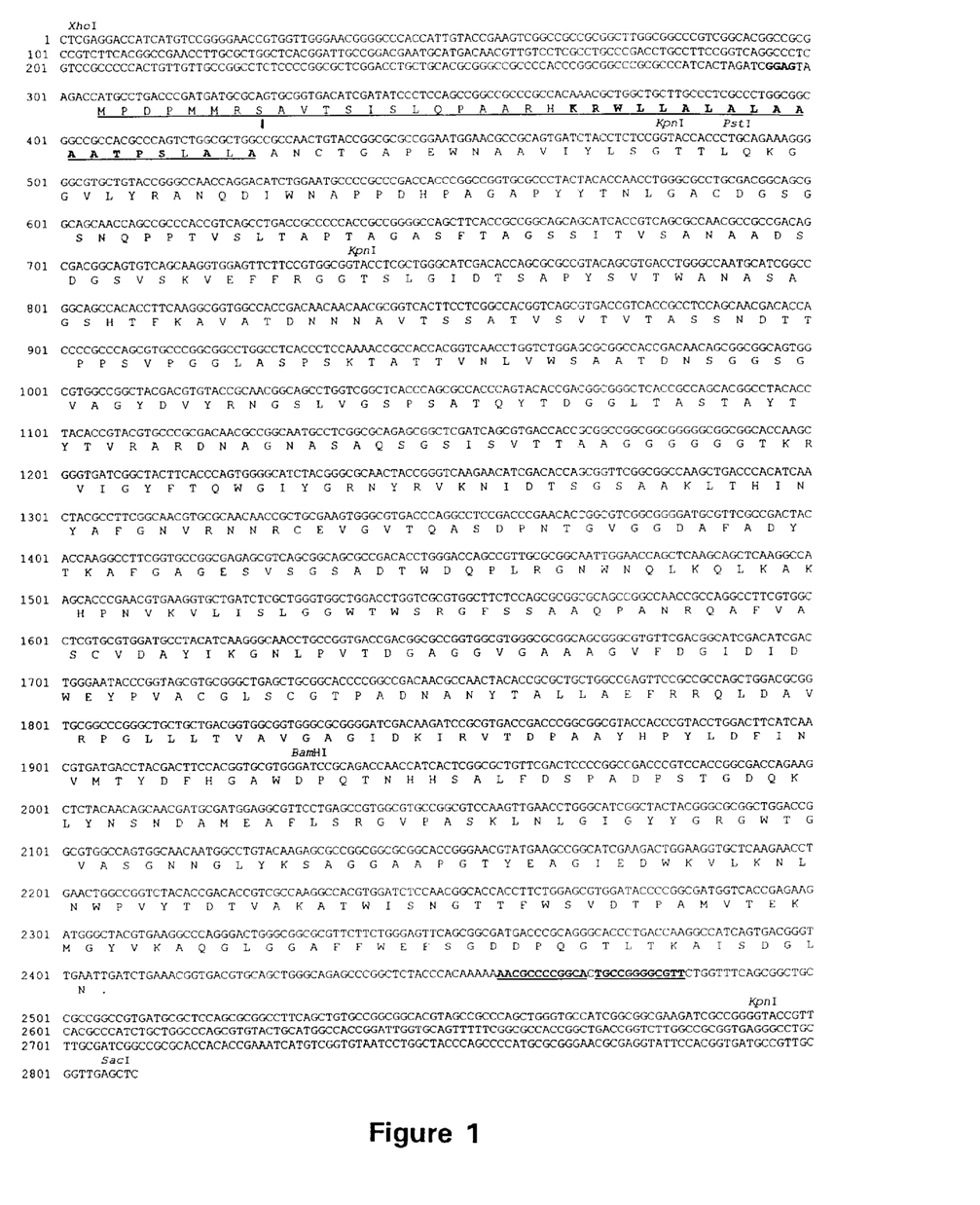

Nucleotide sequence analysis of the chitinase gene from Sm34S1. The nucleotide sequence of the 2.8 kb DNA fragment revealed a large open reading frame (ORFI) of 2100 bases beginning at a predicted start ATG codon located at base 306 that is preceded by a purine rich sequence resembling a ribosome binding site (FIG. 1). Using this start codon, a predicted translation product was deduced that consisted of a 700 amino acid protein with a molecular weight of 72.4 kDa. A 12 base inverted repeat resembling a transcriptional termination sequence was identified 51 bases after the stop codon at base 2457.

Analysis of the first 41 residues of the deduced translation product revealed sequences that are similar to signal peptides (FIG. 1). These include amino acid sequences that share some resemblance to the three domains (N, H and C) constituting classic features of a standard signal peptide (Pugsley, 1993, Microbiol. Rev. 57:50–108). The H or hydrophobic domain, is represented by an 11 amino acid sequence of WLLALALAAAA (SEQ ID NO:2), which begins at the 24th residue. The amino acids KR immediately precedes the H domain, and represents a portion of the N domain that is characteristically polar and carries a net positive charge. The sequence TPSLALAA (SEQ ID NO:2) follows the H domain, and represents the C domain that contains the turn-inducing amino acid, P, at position −6 and the small amino acid, A, at positions −1 and −3 relative to the predicted cleavage site between the last two A residues. Cleavage at this site results in a protein with a predicted size of 68 kDa.

A second large ORF (ORFII) was also observed within the coding region of ORFI. ORFII consisted of 1848 bases, beginning at base 314. In contrast to ORFI, however, ORFII lacked a detectable translation start codon preceded by sequences resembling a ribosome binding site near its beginning. The DNA sequence spanning the region that encoded for both ORFI and ORFII contained a G+C content of >68%.

When the predicted translational products of both ORFI and ORFII were searched within databases, significant sequence identities were detected between the ORFI protein and several chitinases found in the database. In contrast, no homologies revealing significant sequence similarities were detected for ORFII, confirming that ORFI encodes the chitinase gene, designated chiA. The highest degrees of sequence similarities were matched to genes derived from organisms with equivalently high %G+C content. Using the Clustal method of alignment (GCG Software), which assumes no evolutionary relatedness, overall sequence similarities included 41.7% to the chi40 gene product of *Streptomyces thermoviolaceus* (Tsujibo, et al., 1993), 37.2% to the chtA gene product of *S. plicatus* (Robbins, et al., 1992, Gene 111:69–76), 37% to the chiC gene product of *S. lividans* (Fujii, et al. 1993, J. Gen. Microbiol. 139:67–686) and 35.6% to the chi69 gene product of *Janthinobacterium lividum* (Gleave, et al., 1995, FEMS Microbiol. Let. 131:279–288). Respectively lower sequence similarities existed with chitinase gene products originating from organisms containing a corresponding lower %G+C content (data not shown).

Generation of chiA mutant C5 of *S. maltophilia*. Saturation mutagenesis of pXM7B5 using λ::Tn5 resulted in the isolation of over 400 individual plasmids that gained resistance to Km. Each of the 400 plasmids were mobilized into *B. cepacia* M53 and screened for loss of chitinase activity on chitin agar medium. One clone, designated pXM7B5::Tn5-1, was identified that lacked chitinase activity. Restriction map and Southern blot analyses of this plasmid using sequences internal to Tn5 as a probe indicated a transposon insertion into a 250 bp KpnI fragment internal to the ORF that encoded the chitinase gene.

The mutation PXM7B5::Tn5-1 was introduced into the genome of *S. maltophilia* 34S1 by site-directed, marker exchange mutagenesis. A single isolate, designated C5, was identified that expressed resistance to Km at 100 mg/ml, and was verified by Southern blot analysis to contain Tn5 in the 250 bp KpnI fragment. C5 no longer expressed chitinase activity when screened on chitin agar media.

Figure 2:
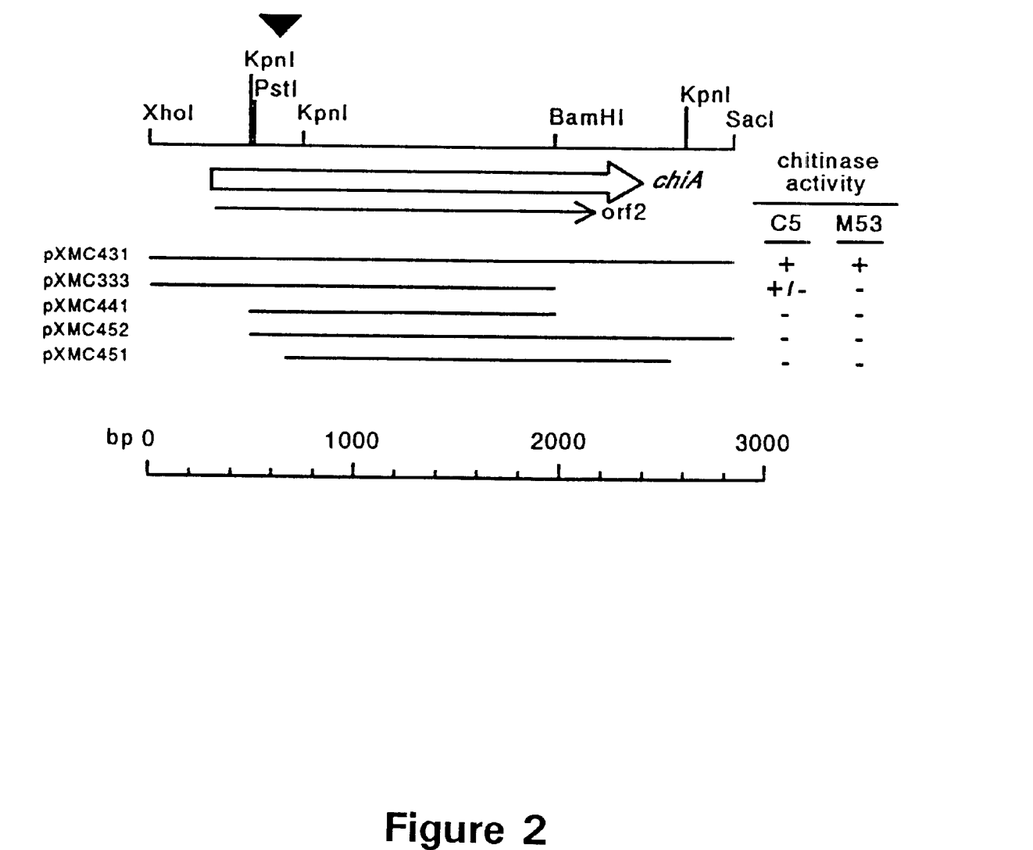
FIG. 2. Restriction map of the 2.8 kb XhoI-SacI fragment, relative positions of constructs and their chitinase activity. Arrows below restriction map indicate position of ORFI encoding the chitinase gene (boxed) and ORFII (solid line). Lines preceded by plasmid names positioned below arrows represent fragments used for plasmid constructs. Each line is followed by enzyme activity in *Stenotrophomonas maltophilia* C5 (chitinase mutant) and *Burkholderia cepacia* M53. (+) represents detected chitinase activity, (−) represents no detected chitinase activity, as determined by clearing zones on colloidal chitin agar. The triangle represents the approximate location of Tn5 which abolishes chitinase activity in pXM7B5 and mutant C5.

Chitinase expression of subclones in *S. maltophilia* C5 and *B. cepacia* M53. Truncated versions of the 2.8 kb XhoI-SacI fragment were subcloned into broad host range vectors to verify chitinase activity with respect to ORFI. In most cases, the success of subcloning experiments appeared dependent upon orienting fragments so that ORFI was positioned opposite to lacZ promoters located in plasmid vectors. Two exceptions to these observations involved the construction of plasmids pXMC431 and pXMC452. In the construction of pXMC431, ORFI contained on the 2.8 kb XhoI-SacI fragment was positioned in the same transcriptional direction as the lacZ promoter in pRK415. pXMC452 was derived from pXMC431 by deleting a 0.5 kb PstI fragment extending from the PstI site located in the polylinker of pXMC431 to a PstI site located 182 bases downstream from the predicted start ATG of ORFI (FIG. 2).

The 2.1 kb KpnI fragment located within the 2.8 kb XhoI-SacI fragment was subcloned into pRK415, resulting in pXMC441. This construct represented a truncation of 437 bases from the predicted start ATG codon at the 5' end of ORFI (FIG. 2). To construct a 476 base truncation from the 3' end of ORFI, the 1.9 kb XhoI-BamHI fragment was excised from pXMC131, using the HindIII site located in the vector polylinker (which externally flanks the XhoI site) and the BamHI site that is located internal to the predicted chitinase ORF. This fragment was ligated into pLAFR3 and designated pXMC333.

Mobilization of various constructs into C5 and detection of chitinase activity were consistent with the predicted chitinase ORF. The 2.8 kb XhoI-SacI fragment in pXMC431 restored chitinase activity to C5 as expected from results observed in *B. cepacia* M53. However, no chitinase activity was detected in either C5 or B. cepacia M53 that contained constructs (pXMC441, pXMC451, and pXMC452) representing deletions within the 5' region of the predicted chiA ORF (FIG. 2). Chitinase activity was not detected with *B. cepacia* M53 containing pXMC333, which represented a 472 bp 3' truncation of ORFI; however, low level of chitinase activity, which appeared visually less than that produced by the wild type strain Sm34S1, was repeatedly detected upon mobilization of pXMC333 into C5. It is possible that the detected chitinase activity in C5(pXMC333) was due to reversions of the Tn5 mutation in the genome by recombination with the homologous region provided by the plasmid, although plasmids representing intact pXMC333 were readily recovered from C5 transconjugants (data not presented).

Characterization of the major chitinase protein from *S. maltophilia*. Sm34S1(pRK415), C5(pRK415), and C5(pXMC431) were grown for three days in M9 broth supplemented with colloidal chitin, and concentrated cell-free culture filtrates were analyzed. SDS-PAGE resolved a major protein band of ca. 47.5 kDa that was present in cultures of Sm34S1 and C5(pXMC431), but was lacking in C5(pRK415).

Native protein gels containing either 4-MU-(GlcNAc)$_2$ or 4-MU-(GlcNAc)$_3$ resolved an identical major band of chitinase activity in culture filtrates of Sm34S1 and C5(pXMC431), but not in culture filtrates of C5. Excision of the active band observed on native gels, followed by electrophoresis on denaturing gels, indicated that chitinase activity corresponded in size with the 47.5 kDa protein located in culture filtrates.

Figure 3:
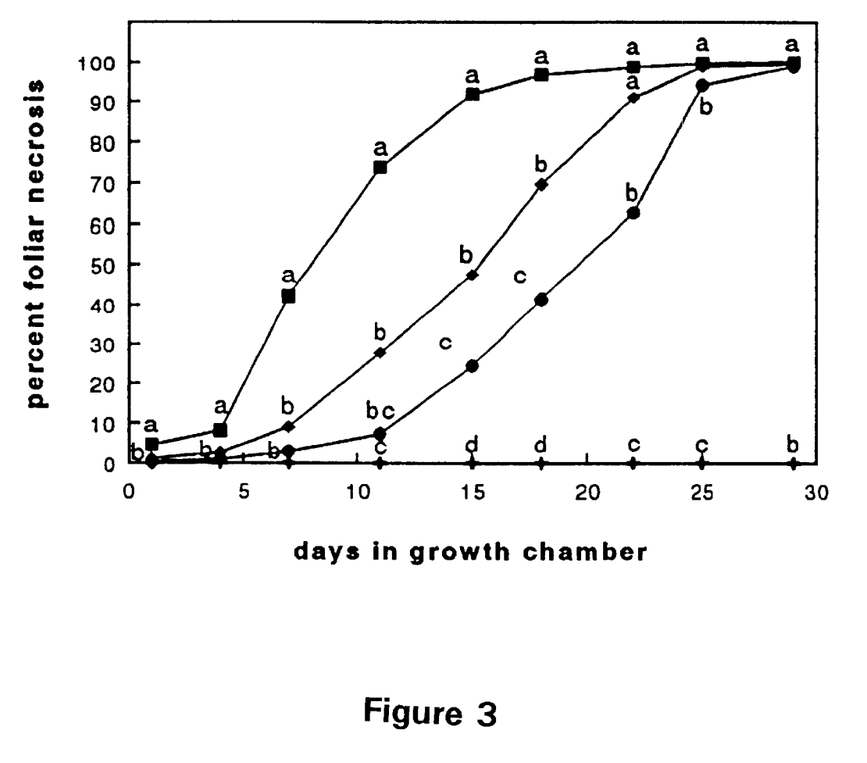

Biological control of summer patch and rhizosphere populations by *S. maltophilia* strains 34S1 and C5. The chiA mutant C5 was compared to Sm34S1 in biocontrol assays against summer patch disease in five separate experimental trials. FIG. 3 represents a single experiment (trial II) illustrating progression of summer patch disease in both bacterial-treated and untreated Kentucky bluegrass plants. Typically, disease progression in both treated and untreated plants followed a sigmoidal shape curve. The rate at which disease progresses in plants receiving various treatments appeared similar; however, the onset of disease in plants treated with Sm34S1 was delayed, resulting in significant reductions in disease on specific observation dates. In experimental trial II, disease in plants treated with C5 progressed in a similar manner to those treated with Sm34S1; however, disease onset was not delayed as extensively. As a result, disease in C5-treated plants were significantly reduced compared to untreated control plants in six of nine observation dates, but were also significantly higher compared to Sm34S1-treated plants on four of nine observation dates (FIG. 3).

Similar trends were observed in four additional experimental trials, although significant differences were not observed in all cases. Table 2 presents results from the single observation date that reflects the largest difference in mean values for summer patch disease ratings between untreated control plants and

TABLE 2

The effect of bacterial treatment on summer patch disease on Kentucky bluegrass var. Baron conducted in the growth chamber.

| Treatment | Experimental trial* | | | | |
|---|---|---|---|---|---|
| | I | II | III | IV | V |
| uninoculated | 0.00[d] | 0.00[d] | 0.00[d] | 0.60[c] | 0.00[c] |
| 34S1 | 52.05b[c] | 24.35[c] | 47.00[c] | 37.15[b] | 58.20[b] |
| C5 | 58.75b[c] | 47.40[b] | 74.50[ab] | 51.30[b] | 68.25[b] |
| Disease control | 76.65[a] | 91.85[a] | 83.95[a] | 84.30[a] | 96.90[a] |

*Results represent the means of disease ratings from 10 replicates on the date in which the greatest difference was observed between the wildtype strain Sm34S1 and the disease control. In each experiment, treatment means followed by the same letter are not significantly different according to a protected least significant different test (P = 0.05).

Sm34S1-treated plants in the five separate trials. In two of the five trials (trials II and III), mean values for disease ratings in plants treated with Cs were significantly different from plants treated with Sm34Sl (Table 2). No significant differences were observed between C5- and Sm34S1-treated plants in the remaining three trials; however, in all cases, the mean values for disease ratings were higher in C5-treated plants compared to 34S1-treated plants.

Populations of Sm34S1 and C5 followed similar patterns in the rhizosphere of Kentucky bluegrass. After both strains initially established at $1 \times 10^8$ cfu/g (dry weight) rhizosphere sample, populations steadily decreased to similar populations below $1 \times 10^6$ cfu/g sample on five observation dates over a two week period. No significant differences were detected between C5 and Sm34S1 on any of the five observation dates during this period in three separate experiments.

DISCUSSION

Characterization of the chiA gene from *S. maltophilia* 34S1 resulted in several unexpected observations. It was difficult to effectively express chiA in *E. coli,* but expression was easily detected in *B. cepacia*. This is thought to be due, in part, to a similarity in %G+C content between *B. cepacia* and *S. maltophilia,* possibly reflecting better adaptation to codon usage. Results from homology searches in databases appear to support this explanation, since they indicate that the Sm34S1 chiA gene product shares the highest levels of overall amino acid sequence similarities with chitinases from organisms of similar high %G+C content. In another interesting observation, subcloning experiments were consistent with the deduced chiA ORF and the predicted translation start site. Sequences strongly resembling a signal peptide predicted a cleavage site located 41 residues from the start ATG, providing a final protein size of 68 kDa. This predicted size of the chiA translational product, however, is not in agreement with the size of the active protein deduced from protein gels. Although the transport of secreted proteins have not been extensively studied in *S. maltophilia,* it may be possible that additional processing occurs and is required to produce an active, mature protein. Chitinase activity in whole cell extracts of *B. cepacia* M53 was detected at a size larger than 68 kDa and in better agreement with the predicted protein size, suggesting this strain lacks the appropriate machinery to process the enzyme to its mature state.

Probably the most surprising observation was made with the sequence analysis of chiA, which revealed the presence of a second, large ORF of over 1800 bp, positioned in the same translational direction, within the coding region of the gene. Database searches revealed no significant similarities between the predicted protein and any known gene product. However, based on the size of the ORF alone, it is possible that ORFII produces the a translational product.

Based on our observations, chitinolytic activity in Sm34S1 is due to the single structural gene, chia, since mutation of this gene in Sm34S1 results in complete loss of enzymatic activity. Biocontrol assays of summer patch disease also provide a strong indication that the chitinase mutant C5 behaves differently than Sm34S1 in controlling summer patch.

It is apparent that chitinase contributes to biocontrol activity of Sm34S1 to some degree, but likely is not the only mechanism that is operating in this system. *S. maltophilia* strains are known to produce several extracellular enzymes (O'Brien and Davis, 1982, J. Clin. Microbiol. 16:417–421; Ordentlich, et al., 1988, Phytopathology 78:84–88), and antibiotic-like compounds (Jakobi and Winkelmann, 1996, J. Antibiotics 49:1101–1104) they may likely also contribute to biocontrol activity. C5 was not significantly impaired in short term persistence in the turfgrass rhizosphere compared to Sm34S1. Furthermore, the mutation did not significantly affect long term rhizosphere or soil populations, providing evidence that the contribution of chitinase to biocontrol activity most likely results by directly affecting the pathogen, and not by loss of ecological fitness.

The present invention is not limited to the embodiments described and exemplified above, but is capable of variation and modification without departure from the scope of the appended claims.

What is claimed:

1. An isolated nucleic acid molecule from *Stenotrophomonas maltophilia* strain 34S1 that comprises SEQ ID NO: 1, that encodes a chitinase and, confers to bacteria that express the nucleic acid, the ability to reduce or prevent summer patch disease and rhizosphere populations caused by fungal plant pathogens.

2. An isolated nucleic acid molecule having:
   a) SEQ ID NO:1; or
   b) a sequence encoding SEQ ID NO:2.

3. An expression cassette, comprising the nucleic acid molecule of claim 2 operably linked to a promoter.

4. A replicative cloning vector, which comprises the isolated nucleic acid molecule of claim 2, and an origin of replication operative in a host cell.

5. A transformed with an isolated nucleic acid molecule of claim 2.

6. The cell of claim 5, which is selected from the group consisting of bacterial cells, yeast cells and plant cells.

7. The biologically pure culture of the cell of claim 5.

* * * * *

SEQUENCE LISTING

<160> NUMBER OF SEQ ID NOS: 2

<210> SEQ ID NO 1
<211> LENGTH: 2810
<212> TYPE: DNA
<213> ORGANISM: Stenotrophomonas maltophilia
<220> FEATURE:
<221> NAME/KEY: CDS
<222> LOCATION: (306)...(2405)
<223> OTHER INFORMATION: Open reading frame 1 (ORFI)
<221> NAME/KEY: sig_peptide
<222> LOCATION: (306)...(428)
<221> NAME/KEY: terminator
<222> LOCATION: (2457)...(2481)
<221> NAME/KEY: RBS
<222> LOCATION: (295)...(298)
<221> NAME/KEY: CDS
<222> LOCATION: (314)...(2162)
<223> OTHER INFORMATION: Open reading frame 2 (ORFII)
<300> PUBLICATION INFORMATION:
<308> DATABASE ACCESSION NUMBER: Genbank No. AF 014950
<309> DATABASE ENTRY DATE: 1997-09-23

<400> SEQUENCE: 1

```
ctcgaggacc atcatgtccg gggaaccgtg gttgggaacg gggcccacca t tgtaccgaa    60 gtcggccgcc gcggcttggc ggcccgtcgg cacggccgcg ccgtcttcac g gccgaacct   120 tgcgctggct cacggattgc cggacgaatg catgacaacg ttgtcctcgc c tgcccgacc   180 tgccttccgg tcaggccctc gtccgccccc actgttgttg ccggcctctc c ccggcgctc   240 ggacctgctg cacgcgggcc gccccacccg gcggcccgcg cccatcacta g atcggagta   300 agacc atg cct gac ccg atg atg cgc agt gcg gtg aca tcg ata tcc ctc   350
      Met Pro Asp Pro Met Met Arg Ser Ala Val Thr Ser Ile Ser Leu
           -40                 -35                 -30 cag ccg gcc gcc cgc cac aaa cgc tgg ctg c tt gcc ctc gcc ctg gcg   398
Gln Pro Ala Ala Arg His Lys Arg Trp Leu L eu Ala Leu Ala Leu Ala
    -25                 -20                 -15 gcg gcc gcc acg ccc agt ctg gcg ctg gcc g cc aac tgt acc ggc gcg   446
Ala Ala Ala Thr Pro Ser Leu Ala Leu Ala A la Asn Cys Thr Gly Ala
-10                  -5                  1                5 ccg gaa tgg aac gcc gca gtg atc tac ctc t cc ggt acc acc ctg cag   494
Pro Glu Trp Asn Ala Ala Val Ile Tyr Leu S er Gly Thr Thr Leu Gln
             10                  15                  20 aaa ggg ggc gtg ctg tac cgg gcc aac cag g ac atc tgg aat gcc ccg   542
Lys Gly Gly Val Leu Tyr Arg Ala Asn Gln A sp Ile Trp Asn Ala Pro
        25                  30                  35 ccc gac cac ccg gcc ggt gcg ccc tac tac a cc aac ctg ggc gcc tgc   590
Pro Asp His Pro Ala Gly Ala Pro Tyr Tyr T hr Asn Leu Gly Ala Cys
    40                  45                  50 gac ggc agc ggc agc aac cag ccg ccc acc g tc agc ctg acc gcc ccc   638
Asp Gly Ser Gly Ser Asn Gln Pro Pro Thr V al Ser Leu Thr Ala Pro
55                  60                  65                  70 acc gcc ggg gcc agc ttc acc gcc ggc agc a gc atc acc gtc agc gcc   686
Thr Ala Gly Ala Ser Phe Thr Ala Gly Ser S er Ile Thr Val Ser Ala
                 75                  80                  85 aac gcc gcc gac agc gac ggc agt gtc agc a ag gtg gag ttc ttc cgt   734
Asn Ala Ala Asp Ser Asp Gly Ser Val Ser L ys Val Glu Phe Phe Arg
            90                  95                 100 ggc ggt acc tcg ctg ggc atc gac acc agc g cg ccg tac agc gtg acc   782
Gly Gly Thr Ser Leu Gly Ile Asp Thr Ser A la Pro Tyr Ser Val Thr
       105                 110                 115 tgg gcc aat gca tcg gcc ggc agc cac acc t tc aag gcg gtg gcc acc   830
```

-continued

```
Trp Ala Asn Ala Ser Ala Gly Ser His Thr Phe Lys Ala Val Ala Thr
            120                 125                 130 gac aac aac aac gcg gtc act tcc tcg gcc acg gtc agc gtg acc gtc        878
Asp Asn Asn Asn Ala Val Thr Ser Ser Ala Thr Val Ser Val Thr Val
135                 140                 145                 150 acc gcc tcc agc aac gac acc acc ccg ccc agc gtg ccc ggc ggc ctg        926
Thr Ala Ser Ser Asn Asp Thr Thr Pro Pro Ser Val Pro Gly Gly Leu
                155                 160                 165 gcc tca ccc tcc aaa acc gcc acc acg gtc aac ctg gtc tgg agc gcg        974
Ala Ser Pro Ser Lys Thr Ala Thr Thr Val Asn Leu Val Trp Ser Ala
            170                 175                 180 gcc acc gac aac agc ggc ggc agt ggc gtg gcc ggc tac gac gtg tac       1022
Ala Thr Asp Asn Ser Gly Gly Ser Gly Val Ala Gly Tyr Asp Val Tyr
                185                 190                 195 cgc aac ggc agc ctg gtc ggc tca ccc agc gcc acc cag tac acc gac       1070
Arg Asn Gly Ser Leu Val Gly Ser Pro Ser Ala Thr Gln Tyr Thr Asp
200                 205                 210 ggc ggg ctc acc gcc agc acg gcc tac acc tac acc gta cgt gcc cgc       1118
Gly Gly Leu Thr Ala Ser Thr Ala Tyr Thr Tyr Thr Val Arg Ala Arg
215                 220                 225                 230 gac aac gcc ggc aat gcc tcg gcg cag agc ggc tcg atc agc gtg acc       1166
Asp Asn Ala Gly Asn Ala Ser Ala Gln Ser Gly Ser Ile Ser Val Thr
                235                 240                 245 acc gcg gcc ggc ggc ggg ggc ggc ggc acc aag cgg gtg atc ggc tac       1214
Thr Ala Ala Gly Gly Gly Gly Gly Gly Thr Lys Arg Val Ile Gly Tyr
            250                 255                 260 ttc acc cag tgg ggc atc tac ggg cgc aac tac cgg gtc aag aac atc       1262
Phe Thr Gln Trp Gly Ile Tyr Gly Arg Asn Tyr Arg Val Lys Asn Ile
                265                 270                 275 gac acc agc ggt tcg gcg gcc aag ctg acc cac atc aac tac gcc ttc       1310
Asp Thr Ser Gly Ser Ala Ala Lys Leu Thr His Ile Asn Tyr Ala Phe
280                 285                 290 ggc aac gtg cgc aac aac cgc tgc gaa gtg ggc gtg acc cag gcc tcc       1358
Gly Asn Val Arg Asn Asn Arg Cys Glu Val Gly Val Thr Gln Ala Ser
295                 300                 305                 310 gac ccg aac acc ggc gtc ggc ggg gat gcg ttc gcc gac tac acc aag       1406
Asp Pro Asn Thr Gly Val Gly Gly Asp Ala Phe Ala Asp Tyr Thr Lys
                315                 320                 325 gcc ttc ggt gcc ggc gag agc gtc agc ggc agc gcc gac acc tgg gac       1454
Ala Phe Gly Ala Gly Glu Ser Val Ser Gly Ser Ala Asp Thr Trp Asp
            330                 335                 340 cag ccg ttg cgc ggc aat tgg aac cag ctc aag cag ctc aag gcc aag       1502
Gln Pro Leu Arg Gly Asn Trp Asn Gln Leu Lys Gln Leu Lys Ala Lys
                345                 350                 355 cac ccg aac gtg aag gtg ctg atc tcg ctg ggt ggc tgg acc tgg tcg       1550
His Pro Asn Val Lys Val Leu Ile Ser Leu Gly Gly Trp Thr Trp Ser
360                 365                 370 cgt ggc ttc tcc agc gcg gcg cag ccg gcc aac cgc cag gcc ttc gtg       1598
Arg Gly Phe Ser Ser Ala Ala Gln Pro Ala Asn Arg Gln Ala Phe Val
375                 380                 385                 390 gcc tcg tgc gtg gat gcc tac atc aag ggc aac ctg ccg gtg acc gac       1646
Ala Ser Cys Val Asp Ala Tyr Ile Lys Gly Asn Leu Pro Val Thr Asp
                395                 400                 405 ggc gcc ggt ggc gtg ggc gcg gca gcg ggc gtg ttc gac ggc atc gac       1694
Gly Ala Gly Gly Val Gly Ala Ala Ala Gly Val Phe Asp Gly Ile Asp
            410                 415                 420 atc gac tgg gaa tac ccg gta gcg tgc ggg ctg agc tgc ggc acc ccg       1742
Ile Asp Trp Glu Tyr Pro Val Ala Cys Gly Leu Ser Cys Gly Thr Pro
                425                 430                 435
```

```
gcc gac aac gcc aac tac acc gcg ctg ctg g cc gag ttc cgc cgc cag     1790
Ala Asp Asn Ala Asn Tyr Thr Ala Leu Leu A la Glu Phe Arg Arg Gln
        440                 445                 450 ctg gac gcg gtg cgg ccc ggg ctg ctg ctg a cg gtg gcg gtg ggc gcg     1838
Leu Asp Ala Val Arg Pro Gly Leu Leu Leu T hr Val Ala Val Gly Ala
455                 460                 465                 470 ggg atc gac aag atc cgc gtg acc gac ccg g cg gcg tac cac ccg tac     1886
Gly Ile Asp Lys Ile Arg Val Thr Asp Pro A la Ala Tyr His Pro Tyr
                475                 480                 485 ctg gac ttc atc aac gtg atg acc tac gac t tc cac ggt gcg tgg gat     1934
Leu Asp Phe Ile Asn Val Met Thr Tyr Asp P he His Gly Ala Trp Asp
            490                 495                 500 ccg cag acc aac cat cac tcg gcg ctg ttc g ac tcc ccg gcc gac ccg     1982
Pro Gln Thr Asn His His Ser Ala Leu Phe A sp Ser Pro Ala Asp Pro
        505                 510                 515 tcc acc ggc gac cag aag ctc tac aac agc a ac gat gcg atg gag gcg     2030
Ser Thr Gly Asp Gln Lys Leu Tyr Asn Ser A sn Asp Ala Met Glu Ala
520                 525                 530 ttc ctg agc cgt ggc gtg ccg gcg tcc aag t tg aac ctg ggc atc ggc     2078
Phe Leu Ser Arg Gly Val Pro Ala Ser Lys L eu Asn Leu Gly Ile Gly
535                 540                 545                 550 tac tac ggg cgc ggc tgg acc ggc gtg gcc a gt ggc aac aat ggc ctg     2126
Tyr Tyr Gly Arg Gly Trp Thr Gly Val Ala S er Gly Asn Asn Gly Leu
                555                 560                 565 tac aag agc gcc ggc ggc gcg gca ccg gga a cg tat gaa gcc ggc atc     2174
Tyr Lys Ser Ala Gly Gly Ala Ala Pro Gly T hr Tyr Glu Ala Gly Ile
            570                 575                 580 gaa gac tgg aag gtg ctc aag aac ctg aac t gg ccg gtc tac acc gac     2222
Glu Asp Trp Lys Val Leu Lys Asn Leu Asn T rp Pro Val Tyr Thr Asp
        585                 590                 595 acc gtc gcc aag gcc acg tgg atc tcc aac g gc acc acc ttc tgg agc     2270
Thr Val Ala Lys Ala Thr Trp Ile Ser Asn G ly Thr Thr Phe Trp Ser
600                 605                 610 gtg gat acc ccg gcg atg gtc acc gag aag a tg ggc tac gtg aag gcc     2318
Val Asp Thr Pro Ala Met Val Thr Glu Lys M et Gly Tyr Val Lys Ala
615                 620                 625                 630 cag gga ctg ggc ggc gcg ttc ttc tgg gag t tc agc ggc gat gac ccg     2366
Gln Gly Leu Gly Gly Ala Phe Phe Trp Glu P he Ser Gly Asp Asp Pro
                635                 640                 645 cag ggc acc ctg acc aag gcc atc agt gac g gg ttg aat tgatctgaaa     2415
Gln Gly Thr Leu Thr Lys Ala Ile Ser Asp G ly Leu Asn
            650                 655 cggtgacgtg cagctgggca gagcccggct ctacccacaa aaaaacgccc c ggcactgcc    2475 ggggcgttct ggtttcagcg gctgccgccg gccgtgatgc gctccagcgc g gccttcagc    2535 tgtgccggcg gcacgtagcc gcccagctgg gtgccatcgg cggcgaagat c gccgggta    2595 ccgttcacgc ccatctgctg gcccagcgtg tactgcatgg ccaccggatt g gtgcagttt   2655 ttcggcgcca ccggctgacc ggtcttggcc gcggtgaggg cctgcttgcg a tcggccgcg   2715 caccacaccg aaatcatgtc ggtgtaatcc tggctaccca gccccatgcg c gggaacgcg   2775 aggtattcca cggtgatgcc gttgcggttg agctc                               2810

<210> SEQ ID NO 2
<211> LENGTH: 700
<212> TYPE: PRT
<213> ORGANISM: Stenotrophomonas  maltophilia
<220> FEATURE:
<221> NAME/KEY: SIGNAL
<222> LOCATION: (1)...(41)
<221> NAME/KEY: DOMAIN
```

-continued

```
<222> LOCATION: (196)...(290)
<221> NAME/KEY: DOMAIN
<222> LOCATION: (330)...(483)
<300> PUBLICATION INFORMATION:
<308> DATABASE ACCESSION NUMBER: Genbank No. AF 014950
<309> DATABASE ENTRY DATE: 1997-09-23

<400> SEQUENCE: 2

Met Pro Asp Pro Met Met Arg Ser Ala Val Thr Ser Ile Ser Leu Gln
    -40                 -35                 -30

Pro Ala Ala Arg His Lys Arg Trp Leu Leu Ala Leu Ala Leu Ala Ala
-25                 -20                 -15                 -10

Ala Ala Thr Pro Ser Leu Ala Leu Ala Ala Asn Cys Thr Gly Ala Pro
                -5                   1                   5

Glu Trp Asn Ala Ala Val Ile Tyr Leu Ser Gly Thr Thr Leu Gln Lys
            10                  15                  20

Gly Gly Val Leu Tyr Arg Ala Asn Gln Asp Ile Trp Asn Ala Pro Pro
        25                  30                  35

Asp His Pro Ala Gly Ala Pro Tyr Tyr Thr Asn Leu Gly Ala Cys Asp
40                  45                  50                  55

Gly Ser Gly Ser Asn Gln Pro Pro Thr Val Ser Leu Thr Ala Pro Thr
                60                  65                  70

Ala Gly Ala Ser Phe Thr Ala Gly Ser Ser Ile Thr Val Ser Ala Asn
            75                  80                  85

Ala Ala Asp Ser Asp Gly Ser Val Ser Lys Val Glu Phe Phe Arg Gly
        90                  95                  100

Gly Thr Ser Leu Gly Ile Asp Thr Ser Ala Pro Tyr Ser Val Thr Trp
        105                 110                 115

Ala Asn Ala Ser Ala Gly Ser His Thr Phe Lys Ala Val Ala Thr Asp
120                 125                 130                 135

Asn Asn Asn Ala Val Thr Ser Ser Ala Thr Val Ser Val Thr Val Thr
            140                 145                 150

Ala Ser Ser Asn Asp Thr Thr Pro Pro Ser Val Pro Gly Gly Leu Ala
            155                 160                 165

Ser Pro Ser Lys Thr Ala Thr Thr Val Asn Leu Val Trp Ser Ala Ala
        170                 175                 180

Thr Asp Asn Ser Gly Gly Ser Gly Val Ala Gly Tyr Asp Val Tyr Arg
185                 190                 195

Asn Gly Ser Leu Val Gly Ser Pro Ser Ala Thr Gln Tyr Thr Asp Gly
200                 205                 210                 215

Gly Leu Thr Ala Ser Thr Ala Tyr Thr Tyr Thr Val Arg Ala Arg Asp
                220                 225                 230

Asn Ala Gly Asn Ala Ser Ala Gln Ser Gly Ser Ile Ser Val Thr Thr
            235                 240                 245

Ala Ala Gly Gly Gly Gly Gly Thr Lys Arg Val Ile Gly Tyr Phe
            250                 255                 260

Thr Gln Trp Gly Ile Tyr Gly Arg Asn Tyr Arg Val Lys Asn Ile Asp
        265                 270                 275

Thr Ser Gly Ser Ala Ala Lys Leu Thr His Ile Asn Tyr Ala Phe Gly
280                 285                 290                 295

Asn Val Arg Asn Asn Arg Cys Glu Val Gly Val Thr Gln Ala Ser Asp
                300                 305                 310

Pro Asn Thr Gly Val Gly Gly Asp Ala Phe Ala Asp Tyr Thr Lys Ala
            315                 320                 325

Phe Gly Ala Gly Glu Ser Val Ser Gly Ser Ala Asp Thr Trp Asp Gln
```

-continued

```
                       330              335              340
Pro Leu Arg Gly Asn Trp Asn Gln Leu Lys Gln Leu Lys Ala Lys His
        345              350              355
Pro Asn Val Lys Val Leu Ile Ser Leu Gly Gly Trp Thr Trp Ser Arg
360              365              370              375
Gly Phe Ser Ser Ala Ala Gln Pro Ala Asn Arg Gln Ala Phe Val Ala
            380              385              390
Ser Cys Val Asp Ala Tyr Ile Lys Gly Asn Leu Pro Val Thr Asp Gly
            395              400              405
Ala Gly Gly Val Gly Ala Ala Ala Gly Val Phe Asp Gly Ile Asp Ile
            410              415              420
Asp Trp Glu Tyr Pro Val Ala Cys Gly Leu Ser Cys Gly Thr Pro Ala
        425              430              435
Asp Asn Ala Asn Tyr Thr Ala Leu Leu Ala Glu Phe Arg Arg Gln Leu
440              445              450              455
Asp Ala Val Arg Pro Gly Leu Leu Leu Thr Val Ala Val Gly Ala Gly
                460              465              470
Ile Asp Lys Ile Arg Val Thr Asp Pro Ala Ala Tyr His Pro Tyr Leu
            475              480              485
Asp Phe Ile Asn Val Met Thr Tyr Asp Phe His Gly Ala Trp Asp Pro
            490              495              500
Gln Thr Asn His His Ser Ala Leu Phe Asp Ser Pro Ala Asp Pro Ser
        505              510              515
Thr Gly Asp Gln Lys Leu Tyr Asn Ser Asn Asp Ala Met Glu Ala Phe
520              525              530              535
Leu Ser Arg Gly Val Pro Ala Ser Lys Leu Asn Leu Gly Ile Gly Tyr
                540              545              550
Tyr Gly Arg Gly Trp Thr Gly Val Ala Ser Gly Asn Asn Gly Leu Tyr
            555              560              565
Lys Ser Ala Gly Gly Ala Ala Pro Gly Thr Tyr Glu Ala Gly Ile Glu
        570              575              580
Asp Trp Lys Val Leu Lys Asn Leu Asn Trp Pro Val Tyr Thr Asp Thr
    585              590              595
Val Ala Lys Ala Thr Trp Ile Ser Asn Gly Thr Thr Phe Trp Ser Val
600              605              610              615
Asp Thr Pro Ala Met Val Thr Glu Lys Met Gly Tyr Val Lys Ala Gln
                620              625              630
Gly Leu Gly Gly Ala Phe Phe Trp Glu Phe Ser Gly Asp Asp Pro Gln
            635              640              645
Gly Thr Leu Thr Lys Ala Ile Ser Asp Gly Leu Glu Asn
            650              655
```